(12) United States Patent
Üstüner

(10) Patent No.: US 7,048,748 B1
(45) Date of Patent: May 23, 2006

(54) AUTOMATIC SURGICAL SUTURING INSTRUMENT AND METHOD

(76) Inventor: Emin Tuncay Üstüner, 602 Church St., Mountain View, CA (US) 94041

( * ) Notice: Subject to any disclaimer, the term of this patent is extended or adjusted under 35 U.S.C. 154(b) by 574 days.

(21) Appl. No.: 09/814,422

(22) Filed: Mar. 21, 2001

(51) Int. Cl.
*A61B 17/04* (2006.01)

(52) U.S. Cl. ............................ 606/144; 606/139
(58) Field of Classification Search ............ 606/139, 606/144, 145, 148; 289/2, 12, 15, 17
See application file for complete search history.

(56) References Cited

U.S. PATENT DOCUMENTS

| | | |
|---|---|---|
| 3,949,924 A | 4/1976 | Green |
| RE28,932 E | 8/1976 | Noiles et al. |
| 4,373,530 A | 2/1983 | Kilejian |
| 4,470,532 A | 9/1984 | Froehlich |
| 4,583,670 A | 4/1986 | Alvarado |
| 4,592,355 A | 6/1986 | Antebi |
| 4,592,498 A | 6/1986 | Braun et al. |
| 4,596,249 A | 6/1986 | Freda et al. |
| 4,641,652 A | 2/1987 | Hatterer et al. |
| 4,664,305 A | 5/1987 | Blake, III et al. |
| 4,841,888 A * | 6/1989 | Mills et al. ............ 112/169 |
| 4,935,027 A * | 6/1990 | Yoon ..................... 606/146 |
| 4,957,498 A | 9/1990 | Caspari et al. |
| 4,981,149 A | 1/1991 | Yoon et al. |
| 5,002,563 A | 3/1991 | Pyka et al. |
| 5,084,058 A | 1/1992 | Li |
| 5,087,263 A | 2/1992 | Li |
| 5,123,913 A | 6/1992 | Wilk et al. |
| 5,144,961 A | 9/1992 | Chen et al. |
| 5,152,769 A | 10/1992 | Baber |
| 5,192,287 A | 3/1993 | Fournier et al. |
| 5,201,744 A | 4/1993 | Jones |
| 5,211,650 A | 5/1993 | Noda |
| 5,217,471 A | 6/1993 | Burkhart |
| 5,234,443 A | 8/1993 | Phan et al. |
| 5,234,444 A | 8/1993 | Christondias |
| 5,257,637 A | 11/1993 | El Gazayerli |
| 5,259,846 A | 11/1993 | Granger et al. |
| 5,308,353 A * | 5/1994 | Beurrier ................. 606/144 |
| 5,318,577 A | 6/1994 | Li |
| 5,320,629 A | 6/1994 | Noda et al. |
| 5,330,491 A | 7/1994 | Walker et al. |
| 5,330,503 A | 7/1994 | Yoon |
| 5,364,409 A | 11/1994 | Kuwabara et al. |
| 5,368,599 A | 11/1994 | Hirsh et al. |
| 5,383,877 A | 1/1995 | Clarke |
| 5,392,978 A | 2/1995 | Velez et al. |
| 5,403,330 A | 4/1995 | Tuason |
| 5,403,346 A | 4/1995 | Loeser |
| 5,405,352 A | 4/1995 | Weston |
| 5,417,700 A | 5/1995 | Egan |
| 5,449,367 A | 9/1995 | Kadry |
| 5,470,010 A | 11/1995 | Rothfuss et al. |
| 5,474,565 A | 12/1995 | Trott |
| 5,480,406 A | 1/1996 | Nolan et al. |
| 5,496,334 A | 3/1996 | Klundt et al. |
| 5,507,776 A | 4/1996 | Hempel |
| 5,520,702 A | 5/1996 | Sauer et al. |
| 5,520,703 A | 5/1996 | Essig et al. |

(Continued)

*Primary Examiner*—David O. Reip
*Assistant Examiner*—Bradford C Pantuck
(74) *Attorney, Agent, or Firm*—Brinks Hofer Gilson & Lione

(57) ABSTRACT

A surgical instrument that automatically ties simple interrupted sutures is described. The user adjusts the tension in the suture loop. The instrument can use any of the currently used suture materials. In one form, sutures, a needle and two small blades come in a modular unit that is attached to a main piece. The advantages of conventional suturing are combined with the practicality of a surgical stapler.

35 Claims, 12 Drawing Sheets

U.S. PATENT DOCUMENTS

| | | |
|---|---|---|
| 5,540,705 A | 7/1996 | Meade et al. |
| 5,553,765 A | 9/1996 | Knodel et al. |
| 5,554,169 A | 9/1996 | Green |
| 5,565,122 A | 10/1996 | Zinnbauer et al. |
| 5,569,270 A | 10/1996 | Weng |
| 5,643,293 A * | 7/1997 | Kogasaka et al. .......... 606/148 |
| 5,643,295 A | 7/1997 | Yoon |
| 5,665,096 A * | 9/1997 | Yoon ......................... 606/139 |
| 5,683,417 A | 11/1997 | Cooper |
| 5,697,543 A | 12/1997 | Burdorff |
| 5,716,368 A | 2/1998 | de la Torre et al. |
| 5,725,522 A | 3/1998 | Sinofsky |
| 5,741,279 A | 4/1998 | Gordon et al. |
| 5,746,754 A | 5/1998 | Chan |
| 5,752,964 A | 5/1998 | Mericle |
| 5,766,186 A | 6/1998 | Faraz et al. |
| 5,769,862 A * | 6/1998 | Kammerer et al. ......... 606/148 |
| 5,769,863 A | 6/1998 | Garrison |
| 5,772,672 A | 6/1998 | Toy et al. |
| 5,776,150 A | 7/1998 | Nolan et al. |
| 5,810,852 A | 9/1998 | Greenberg et al. |
| 5,810,855 A | 9/1998 | Rayburn et al. |
| 5,814,054 A | 9/1998 | Kortenbach et al. |
| 5,829,662 A | 11/1998 | Allen et al. |
| 5,846,254 A | 12/1998 | Schulze et al. |
| 5,893,855 A | 4/1999 | Jacobs |
| 5,895,395 A | 4/1999 | Yeung |
| 5,919,208 A | 7/1999 | Valenti |
| 5,931,855 A | 8/1999 | Buncke |
| 5,951,587 A | 9/1999 | Qureshi et al. |
| 5,954,733 A | 9/1999 | Yoon |
| 5,984,933 A | 11/1999 | Yoon |
| 6,010,525 A | 1/2000 | Bonutti et al. |
| 6,045,561 A | 4/2000 | Marshall et al. |
| 6,066,160 A | 5/2000 | Colvin et al. |
| 6,071,289 A | 6/2000 | Stefanchik et al. |
| 6,074,404 A | 6/2000 | Stalker et al. |
| 6,077,277 A | 6/2000 | Mollenauer et al. |
| 6,086,601 A | 7/2000 | Yoon |
| 6,099,553 A | 8/2000 | Hart et al. |
| 6,106,545 A | 8/2000 | Egan |
| 6,221,084 B1 * | 4/2001 | Fleenor ...................... 606/148 |
| 2002/0116011 A1 * | 8/2002 | Chee Chung et al. ...... 606/145 |

* cited by examiner

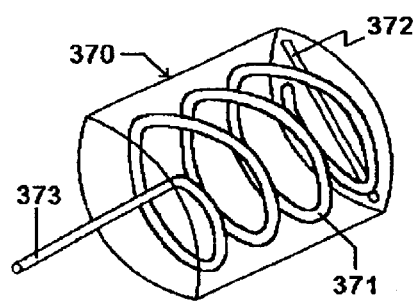
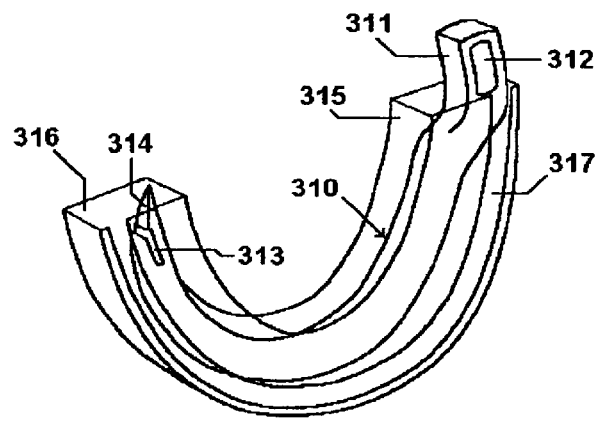
Fig. 2a
Fig. 2b
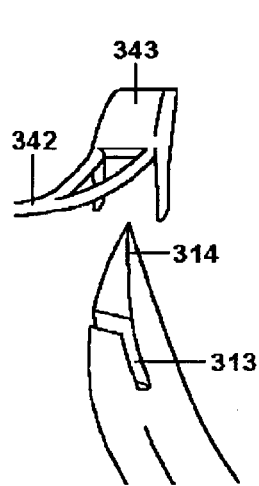
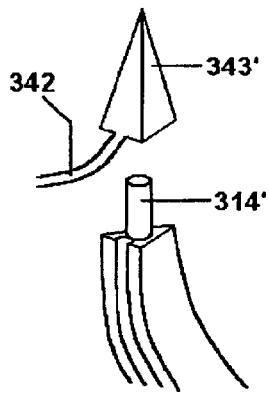
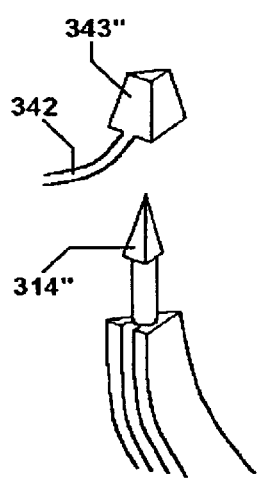
Fig. 2c
Fig. 2d
Fig. 2e

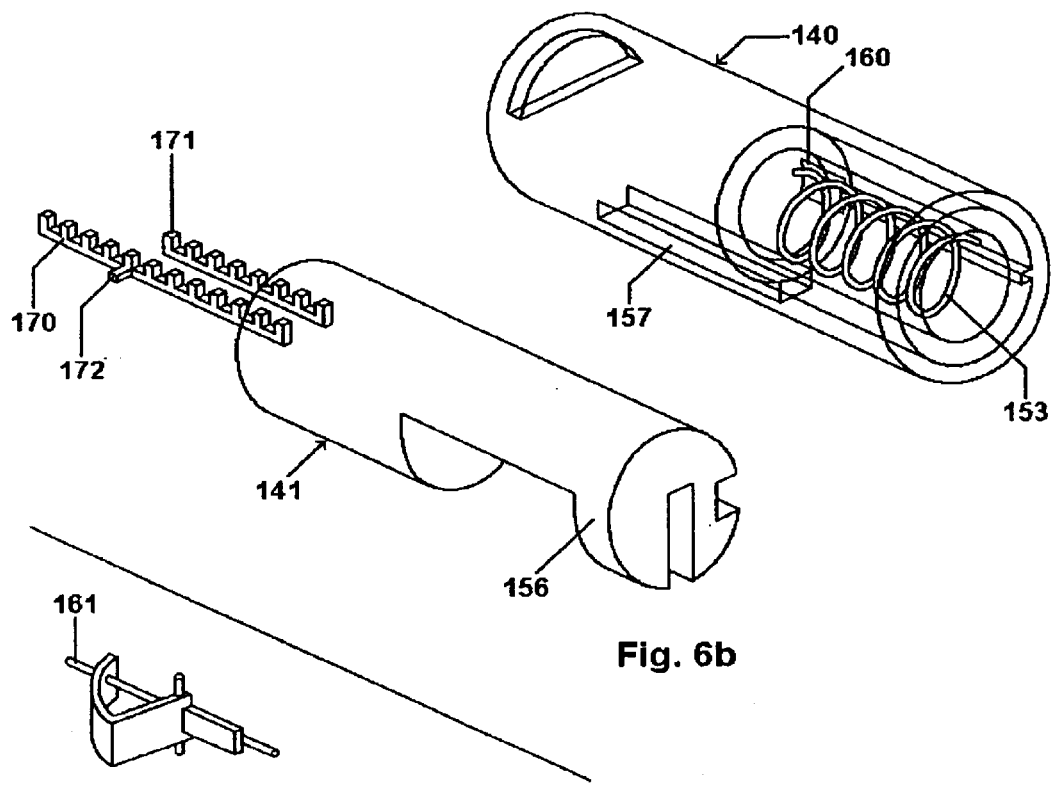
Fig. 6b
Fig. 6c
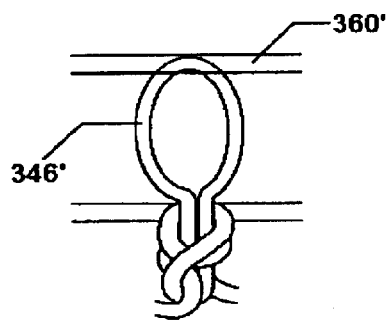
Fig. 7

AUTOMATIC SURGICAL SUTURING INSTRUMENT AND METHOD

BACKGROUND

This invention pertains to an instrument and method for automating the conventional suturing process routinely performed during open and endoscopic surgeries.

Conventional suturing, where a practitioner manually sutures tissues with a needle and suture material, is still the preferred method and has not been replaced by any other technique. However, it is a time consuming process and this inconvenience becomes even more pronounced during endoscopic surgeries.

Most of the time a simple interrupted suture is what is needed, and a surgeon's knot is the type of knot used. In order to tie a simple interrupted suture, a needle, a suture material attached to the needle and three additional instruments are generally used: a needle holder, a forceps and a pair of scissors.

To suture during an open surgical operation, first an assistant takes a needle out of a needle dispenser with a needle holder and then hands the needle holder to the practitioner with the tip of the needle pointing left or right depending on whether the practitioner is right- or left-handed. The practitioner manipulates and positions the tissues or the structures to be sutured with a forceps in his/her other hand and passes the needle and the attached suture material through them. To form a surgeon's knot, first a double-wrap throw is made, followed by a single-wrap throw in the reverse direction. To make a double-wrap throw, the needle-attached end of the suture material is wrapped around the distal body of the needle holder twice in the same direction. The other end of the suture material is grasped with the needle holder to pull through the wrappings made around the needle holder while the needle-attached end of the suture material is pulled in the opposite direction. After desired tension on the tissues or structures within this first loop is attained, the ends of the suture material are released. To make a single-wrap throw, the same process is repeated wrapping around the needle holder only once and in the reverse direction. This creates a second loop, and its size is reduced to a minimum by pulling on the ends of the suture material to secure the knot. Following final tightening the excess lengths of the suture material on both ends are cut, usually by the assisting person.

Endoscopic surgeries, on the other hand, are surgeries performed with the aid of an endoscope, which is basically a video camera. The surgical site is reached through one or more small ports. Special elongated instruments including an endoscope are introduced through these ports. Direct view of the surgical site is not available, but a limited indirect view is provided by the endoscope. Therefore, simple but time-consuming maneuvers described above for an open surgery (such as wrapping a suture material around an instrument, passing the needle from one instrument to another) become more tedious and more time consuming. Incidents such as dropping the needle may become a real issue. Therefore, most of the efforts to advance the state of the art of suturing have been intended to facilitate endoscopic suturing.

Among all the steps of suturing, tying a knot is the lengthiest and the one that involves the most manipulation, and several patents address this step. For example, U.S. Pat. Nos. 5,002,563 (Pyka, et al), 5,259,846 (Granger, et al), 5,368,599 (Hirsh, et al.), 5,403,346 (Loeser), 5,520,702 (Sauer, et al.), 4,592,355 (Antebi), 5,123,913 (Wilk, et al.), 5,330,503 (Yoon), 5,643,295 (Yoon), 4,981,149 (Yoon, et al.), 5,683,417 (Cooper), 5,931,855 (Buncke), 5,984,933 (Yoon), 5,919,208 (Valenti), 6,010,525 (Bonutti, et al.), 6,066,160 (Colvin, et al.), and 6,099,553 (Hart, et al.), are representative of suture devices, or suture materials of special structures designed to avoid forming knots. U.S. Pat. Nos. 5,725,522 (Sinofsky), 5,565,122 (Zinnbauer, et al.), 6,077,277 (Mollenauer, et al.), 5,417,700 (Egan), and 6,106,545 (Egan) suggest using laser radiation or radiant heat to effect fusion instead of tying knots. These patents are mostly for techniques to avoid tying a knot altogether. The ones on facilitating tying knots, on the other hand, are almost exclusively for endoscopic surgeries.

There are at least three ways of tying sutures during an endoscopic surgery. One way is taking both ends of the suture material out after passing it through the tissue and forming the knot extracorporeally and pushing it back inside the surgical field. U.S. Pat. Nos. 5,084,058 (Li), 5,087,263 (Li), 5,257,637 (El Gazayerli), 5,403,330 (Tuason), 5,769,863 (Garrison), 5,234,444 (Christondias), 5,217,471 (Burkhart), and U.S. Pat. No. 5,752,964 (Mericle) are examples of knot pushers. A second way of tying sutures during endoscopic procedures is of course forming and tying knots intracorporeally, which is extremely tedious. However, there are some instruments designed to help tying knots intracorporeally especially for forming loops. U.S. Pat. Nos. 5,192,287 (Fournier, et al.), 5,201,744 (Jones), 5,716,368 (de la Torre, et al.), 5,810,852 (Greenberg, et al.), 5,383,877 (Clarke), 6,045,561 (Marshall, et al.), 6,086,601 (Yoon), 5,234,443 (Phan, et al.), 4,641,652 (Hatterer, et al.), and 5,480,406 (Nolan, et al.) are examples of this class.

Use of preformed knotted loops is the third way of tying sutures during endoscopic surgeries. U.S. Pat. Nos. 5,405,352 (Weston), 5,330,491 (Walker, et al.), 5,449,367 (Kadry), 5,643,293 (Kogasaka, et al.), 5,846,254 (Schulze, et al.), 5,211,650 (Noda), 5,320,629 (Noda, et al.), and 5,144,961 (Chen, et al.) disclose devices using preformed knotted loops or partially tied knots within which the needle is passed and the suture is tied.

There are also patents addressing the steps of suturing other than tying knots, such as manipulation of the needle and suture threading. Some of these inventions also assist forming knots during endoscopic procedures. Others disclose a specific needle or a needle holder design. Some examples of this class of patents are U.S. Pat. Nos. 4,373,530 (Kilejian), 4,164,225 (Johnson, et al.), 4,345,601 (Fukuda), 4,557,265 (Andersson), 4,596,249 (Freda, et al.), 5,318,577 (Li), 5,474,565 (Trott), 5,569,270 (Weng), 5,540,705 (Meade, et al.), 5,520,703 (Essig, et al.), 5,772,672 (Toy, et al.), 5,746,754 (Chan), 5,741,279 (Gordon, et al.), 5,665,096 (Yoon), 4,957,498 (Caspari, et al.), 5,776,150 (Nolan, et al.), 5,766,186 (Faraz, et al.), 5,951,587 (Qureshi, et al.), 5,954,733 (Yoon), 5,152,769 (Baber), 6,074,404 (Stalker, et al.), 6,071,289 (Stefanchik, et al.), 5,814,054 (Kortenbach, et al.), 5,895,395 (Yeung), and 5,364,409 (Kuwabara, et al.)

A particularly successful invention in this field has been the surgical stapler. In some limited set of applications, the surgical stapler has been able to replace conventional suturing for many practitioners. There are quite a number of patents disclosing surgical staplers designed to be used during open surgeries (e.g., U.S. Pat. Nos. 4,470,532 (Froehlich), 5,893,855 (Jacobs), 4,664,305 (Blake, III, et al.), 4,583,670 (Alvarado), RE28,932 (Noiles, et al.), 4,592,498 (Braun, et al.), 3,949,924 (Green), 5,697,543 (Burdorff) or endoscopic surgeries (e.g., U.S. Pat. Nos. 5,392,978 (Velez, et al.), 5,470,010 (Rothfuss, et al.), 5,553,765

(Knodel, et al.), 5,554,169 (Green, et al.), 5,810,855 (Rayburn, et al.), 5,829,662 (Allen, et al.).

Surgical staplers are actually very similar to their office counterparts. They dispatch staples to clip and hold tissue together. The surgical staples, however, can be made of metal or absorbable materials. They are designed to combine the functions of a needle and a suture material in one body. They need to penetrate the tissue like a needle and hold the grasped tissue like a tied suture material. Metal staples may be thought of needles bent and left in tissue. Even though the ends of staples are left free, since they are able to preserve their new shape they fix the tissue edges. Metal staples are not absorbable. Absorbable staples, on the other hand, require an extremely large amount of material to be introduced into the body to provide a secure fastening (see U.S. Pat. No. 5,507,776 (Hempel)).

The reason that staplers have found applications in today's field of surgery is often not because they are superior to conventional suturing in terms of the results they provide, but because it is faster to staple with a simple maneuver. One of the disadvantages of staplers is that the tension applied on the grasped tissue by staples cannot be adjusted. It is sometimes too loose, sometimes too tight. Also scars caused by stapling are usually worse than scars with conventional suturing. This is why staplers are usually used where esthetical results are not sought. In addition many surgeons prefer the security of sutures to staples.

A suturing apparatus described by Klundt, et al. (U.S. Pat. No. 5,496,334) automatically sutures by performing a single-thread overcast stitching operation, like a sewing machine; however this apparatus cannot tie single interrupted sutures.

Therefore, there is a need for an instrument that automates what a practitioner does during a conventional suturing process, which in spite of many recent inventions is often still the preferred method of closing wounds. Such an instrument would preferably combine the practicality of a stapler with the advantages of conventional suturing.

SUMMARY

The preferred embodiment described below is an instrument for suturing tissue in open and endoscopic surgeries, and it ties simple interrupted sutures with non-slip knots in an automatic manner. This embodiment can use all available suture materials used in conventional suturing today, as well as new suture materials developed in the future.

The illustrated embodiment automatically passes suture material through tissue, and then automatically ties a desired type of non-slip knot after passing the suture material through the tissue. This embodiment leaves the adjustment of the tension within the suture loop to the practitioner, and it automatically cuts the extra lengths from the ends of the suture material on both sides of a knot.

This embodiment allows multiple interrupted sutures to be placed without reloading. It executes the above steps sequentially and can repeat them without creating a need for the practitioner to change hands or take the instrument out of the surgical site in endoscopic surgeries.

The foregoing paragraphs have been provided by way of general introduction, and they should not be used to narrow the scope of the following claims.

BRIEF DESCRIPTION OF THE DRAWINGS

FIG. 2a is a schematic diagram of a suture carrier included in the embodiment of FIG. 1b.

FIG. 2b is a perspective view of a needle guide and a needle included in the embodiment of FIG. 1b.

FIGS. 2c, 2d and 2e are perspective views of three alternative arrangements for coupling a suture to the pointed end of the needle of FIG. 2b.

FIGS. 5a and 5b are perspective views illustrating components coupled to the actuators of the embodiment of FIG. 1a.

FIGS. 6a, 6b and 6c illustrate components of the embodiment of FIG. 1a that couple the actuators to the suture delivery system.

FIG. 7 is a schematic representation of an example of a partially tied knot suitable for use with this invention.

DETAILED DESCRIPTION OF THE PREFERRED EMBODIMENTS

Overview

Turning now to the drawings, the operation of the suturing device 100 of FIGS. 1a and 1b will first be described generally using the schematic diagrams of FIGS. 3a through 3f. The discussion will then turn to a detailed description of the structure and operation of the suturing device 100 in its presently preferred form.

Figure 1A:
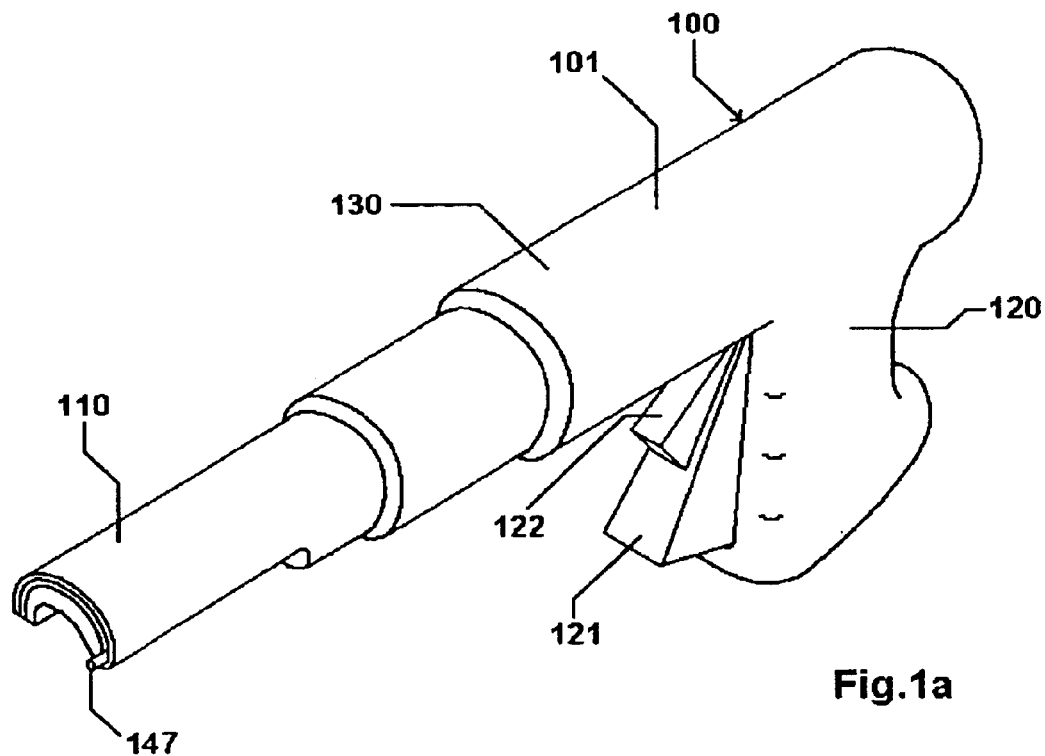
FIG. 1a is a perspective view of a suturing device that incorporates a preferred embodiment of this invention, with the suture delivery module removed.
Figure 1B:
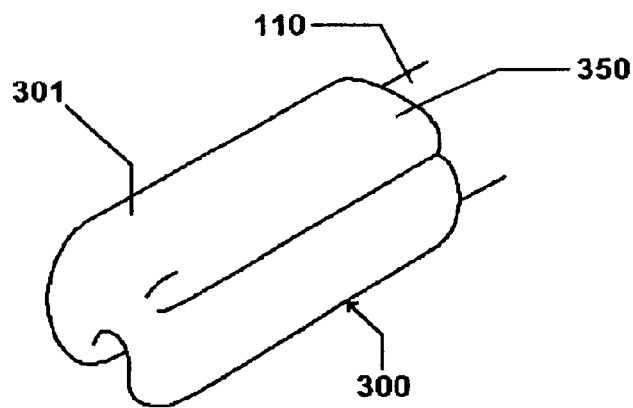
FIG. 1b is a fragmentary perspective view of the suturing device of FIG. 1a, with the suture delivery module installed.

As shown in FIGS. 1a and 1b, the suturing device 100 includes a frame 101 that supports an operating portion 110 and a handle portion 120. The handle portion 120 is intended to be held in the hand of a surgeon, and it includes first and second actuators 121, 122. In this embodiment the actuators 121, 122 pivot in the manner of triggers with respect to the handle portion 120, though other sliding or pivoting motions can also be used.

Figure 2F:
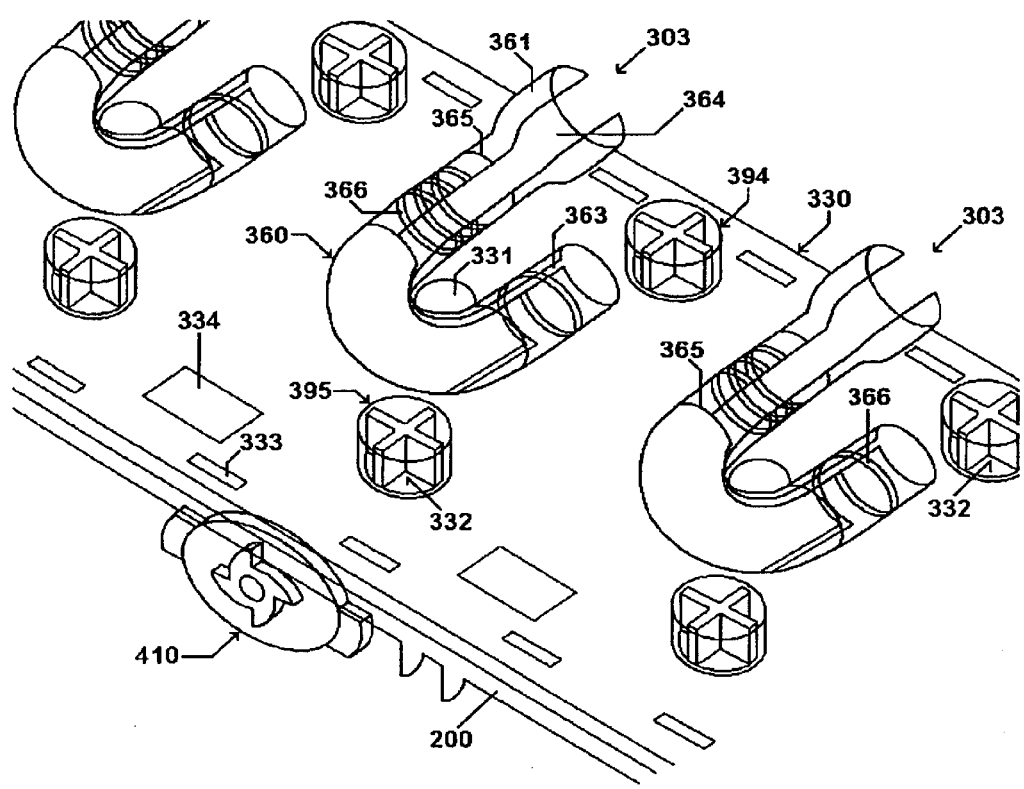
FIG. 2f is a perspective view of a plurality of sutures and associated structures included in the suture delivery system of FIG. 1b.

The operating portion 110 supports at its distal end a removable suture delivery system 300. The suture delivery system 300 includes a modular housing 301 intended to fit over and then to be removed from the operating portion 110. The suture delivery system 300 includes many suture assemblies 303, each mounted on a carrier support 330 (FIG. 2f). The suture delivery system 300 also includes a needle guide 315 that is arcuate in shape and that supports an arcuate needle 310 for sliding movement in the guide 315 (FIG. 2b). The spatial relationship between the needle 310 and the suture assemblies is shown generally in FIG. 2h.

Figure 3A:
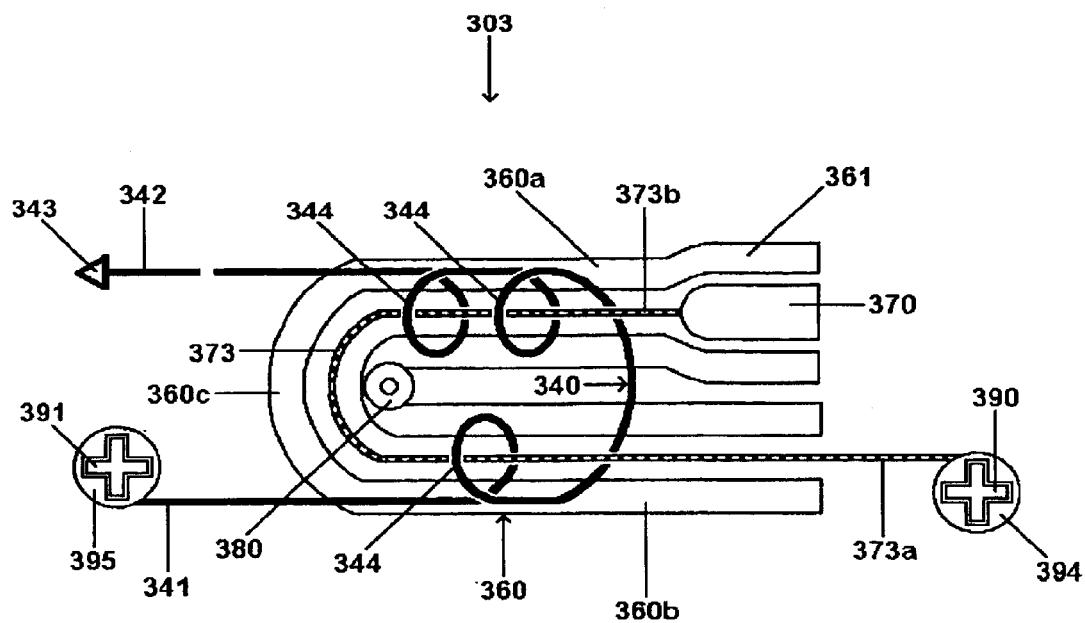
FIGS. 3a through 3f are sequential views illustrating a method for tying a surgeon's knot in a suture. The illustrated method can be implemented with the embodiment of FIGS. 1a and 1b.

The operation of the suturing device 100 can best be understood in general terms with reference to FIGS. 3a–3f. FIG. 3a shows a schematic view of one of the suture assemblies 303 in an initial condition. The suture assembly 303 includes a suture 340 having a first end 341 connected to a spool 395 and a second end 342 connected to an enlarged element 343. The suture 340 is wrapped in a plurality of coils 344 around a tube 360. For example, the tube 360 may have grooves in the walls of the tube to receive the suture 340, and these grooves may be closed at their inner surface by a frangible material.

The tube 360 in this embodiment is U-shaped, and the tube 360 includes a first leg 360a and a second leg 360b interconnected by a bight section 360c.

The suture assembly 303 also includes a suture carrier that includes a line 373 and a gripping element 370. The line 373 has a first end 373a that is connected to a spool 394 and a second end 373b that is connected to the gripping element 370. The gripping element 370 is adapted to grip and hold the enlarged element 343 that is secured to the second end 342 of the suture 340.

The spools 394, 395 are rotatable by respective spool drivers 390, 391, and a spacer 380 is positioned between the two legs 360a, 360b of the tube 360.

In order to initiate the process of tying a suture knot with the suturing device 100, the surgeon positions the suture delivery system 300 appropriately and then squeezes the first actuator 121 to move the needle 310 from its original, retracted position (FIG. 2h) to an extended position, which causes the needle to engage the enlarged element 343 and the associated suture and then to pierce the two tissues to be joined by the suture. When the needle 310 is fully extended in the guide 315, the needle 310 inserts the enlarged element 343 into the gripping element 370 (as shown in FIG. 3b), thereby forming the first loop 345 in the suture.

Figure 3B:
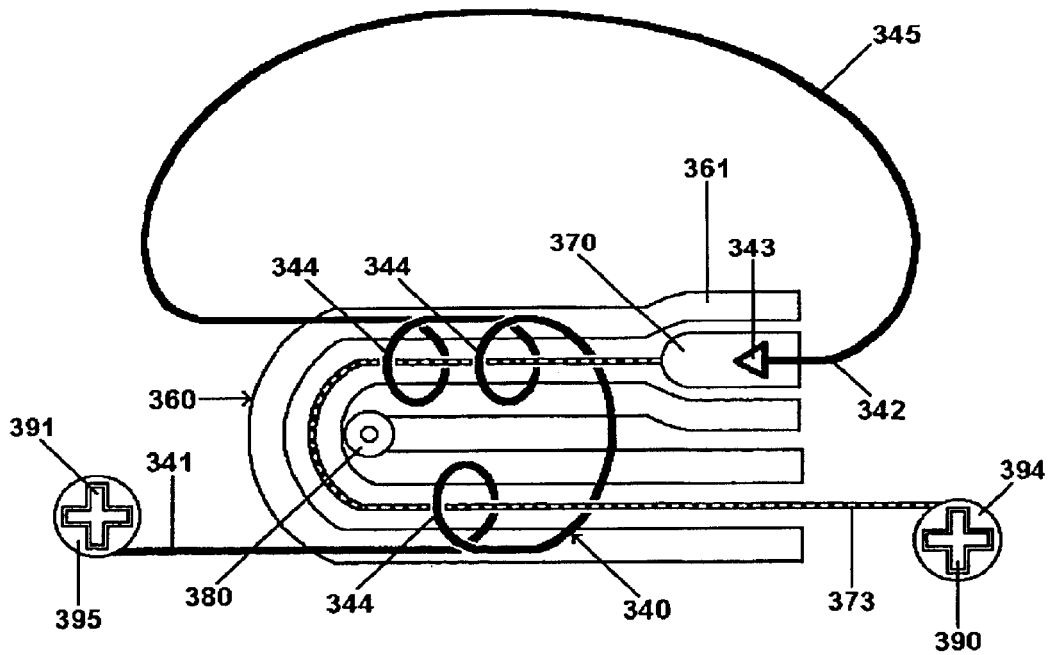
Figure 3C:
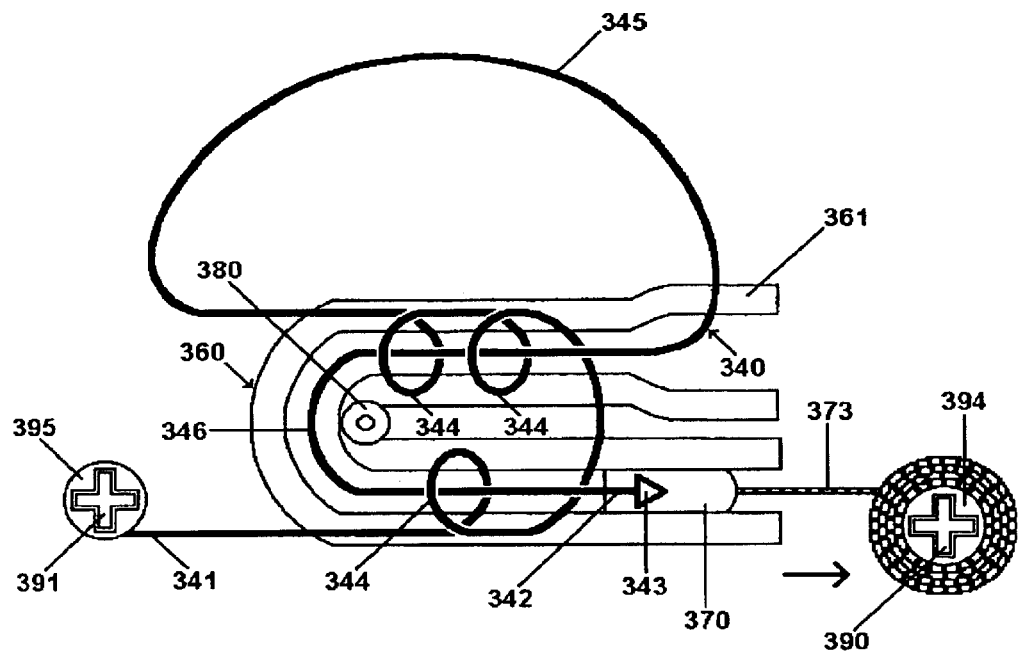

As the surgeon continues depressing the first actuator 121, the suturing device 100 rotates the spool driver 390 and the spool 394, thereby winding the line 373 on the spool 394 and pulling the gripping element 370 and the attached enlarged element 343 through the tube 360, as shown in FIG. 3c. Note that this action causes the second end 342 of the suture 340 to pass through the preformed coils 344 and forms the second loop 346 in the suture. In this text, the term "second loop" also indicates the pre made loop 346' of a partially tied knot (FIG. 7) when a partially tied knot is used, although it is not exactly the same second loop that is obtained with the use of a coiled suture. In both cases the first loop indicates the one that encircles the tissue.

Figure 3D:
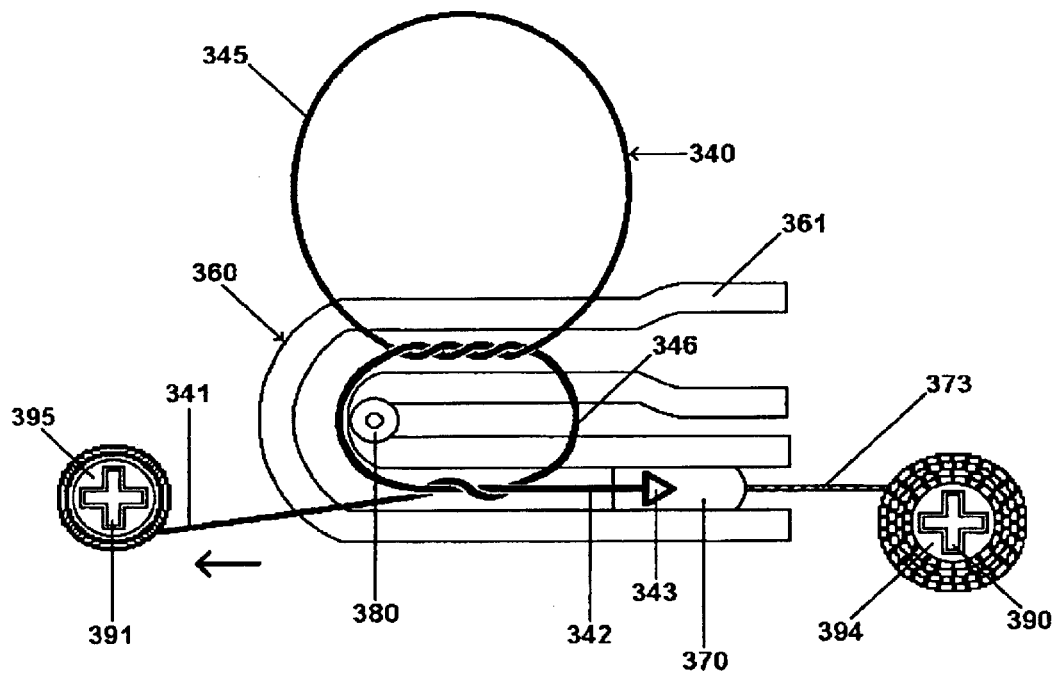
Figure 3E:
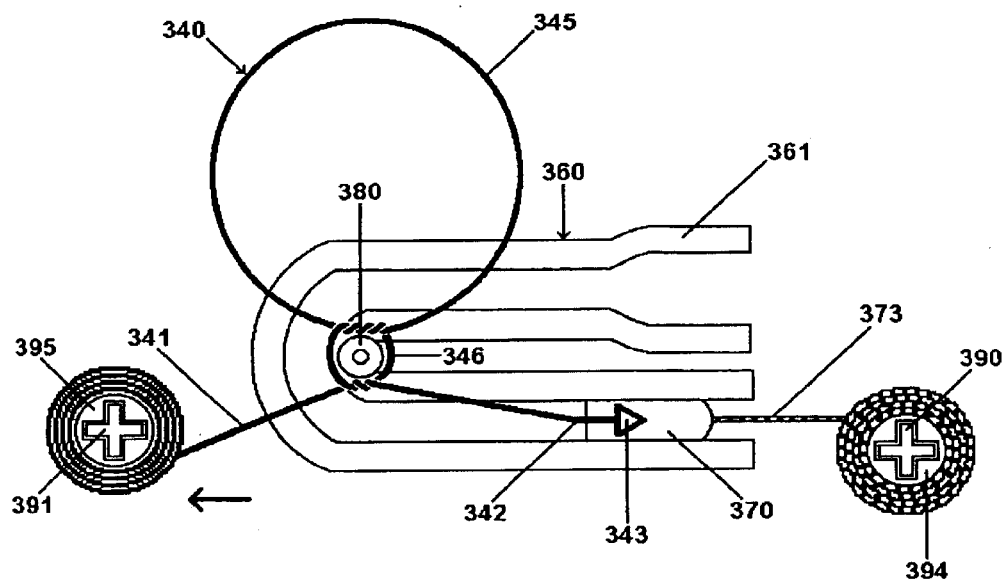

Continued motion of the first actuator 121 causes the suturing device 100 to rotate the spool driver 391 and the spool 395, thereby winding the first end 341 of the suture 340 around the spool 395. This increases the tension second loop 346 of the suture 340, thereby causing the suture 340 to break through the breakable material that makes up the walls of the tube 360. This first brings the preformed coils of the suture 340 into intimate contact with the second end 342 of suture 340, as shown in FIG. 3d and then positions the second loop 346 closely around a spacer 380, as shown in FIG. 3e.

Figure 3F:
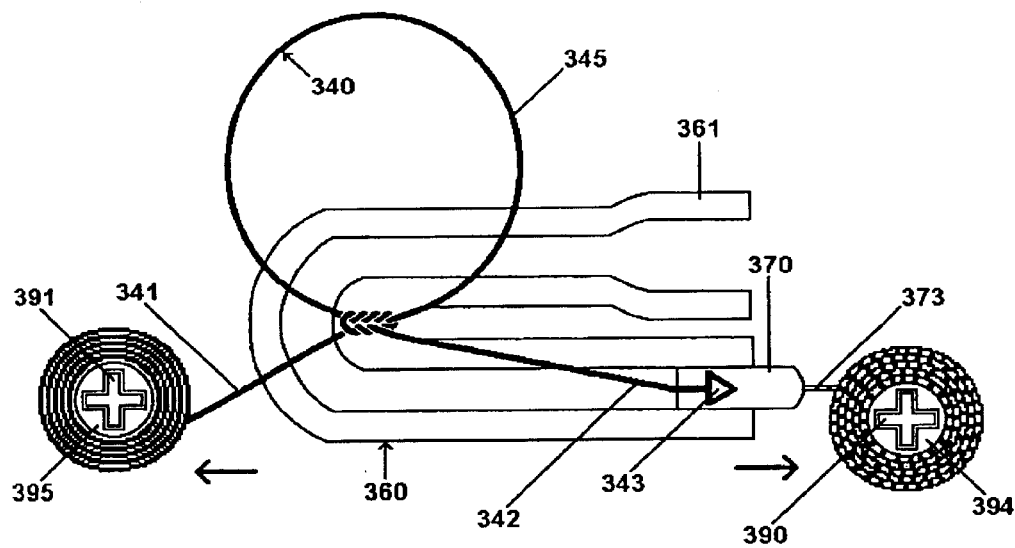

The spacer 380 prevents the loop 346 from tightening on the loop 345 as the loop 345 is itself being tightened and it allows the loops 345, 346 to be tightened independently of one another. When the operation shown in FIG. 3e has continued to the point where an adequate tension is developed in the loop 345 of the suture 340 that passes through the tissue, the surgeon then releases the first actuator 121 and begins to depress the second actuator 122. As a consequence of this actuation, the spacer 380 is removed, and the knot is fully tensioned, as shown in FIG. 3f. As the spacer 380 is pulled out of the loop 346, both ends of the suture are pulled simultaneously applying equal forces in order to tighten the loop 346 and form a non-slip knot. When the spacer 380 is totally removed from the loop 346, the knot becomes secured and the shafts driving the spools 394, 395 are automatically stopped.

Release of the second actuator 122 causes the used suture assembly 303 to be moved out of alignment with the needle guide 315. This motion causes the fully tied knot to move past two trimmer blades 320 that trim the excess suture on both sides of the knot. Release of the second actuator 122 also indexes a next suture assembly into alignment with the needle guide, thereby preparing the suturing device 100 to tie a next suture.

The example of FIGS. 3a–3f illustrates a method for tying a surgeon's knot. This method can readily be adapted to other knots. It is possible to obtain different types of knots by changing the number of coils around the first leg 360a and the second leg 360b of the tube, or by arranging the coils of the sutures around a one-legged tube instead of a two-legged U-shaped tube, or by placing the loop 346' of a partially tied knot around a tube 360' (FIG. 7) instead of wrapping a suture in coils.

Of course, many other variations are possible. For example, in one alternative the end of the suture that is gripped by the gripping element can be wrapped around the other end of the suture by pulling it through a tube that is itself wrapped around the other end of the suture. In this case, the suture carrier is placed in the coiled tube around the suture. As before, the suture end is pulled by the suture carrier to make the desired wraps and create the desired knot. With above examples, it should be apparent that the tube illustrated and discussed above can be straight, curved, U-shaped or coiled. It may or may not be cylindrical in cross-section, and it should be understood that the term "tube" is intended broadly to encompass a wide variety of structures that create the desired canal or passage and support coils or loops of a suture.

The gripping element of the suture carrier may be placed behind or at the same level as the coils of the suture or the loop of the partially tied knot when they are wrapped around a one-legged tube in the direction of movement of the needle tip as it approaches the tube. Where the gripping element is placed behind the coils or the loop, the second end 342 of the suture and the enlarged element 343 are passed through the tube by the needle. In this variation the suture carrier may consist of only a gripping element, which may also work as a spool.

The term "wrapped around " is intended broadly to encompass a wide variety of wrapping arrangements that accomplish the purposes set out above. For example, a suture or a suture carrier may be placed on the outer circumference of the tube, may be placed in inwardly-opening or outwardly-opening grooves in the walls of the tube, or may be placed in suitable slots in the walls of the tube.

FIG. 7 shows an example of a partially tied knot that can be used with the method of this invention. The loop 346' of this partially tied knot is wrapped around a tube 360', which is represented by the double solid horizontal lines. One end of the suture (shown by an arrow) is passed through this loop 346' after it has passed through tissue and before or after it has been gripped by a suture carrier (not shown). The other end of this partially tied suture will be directly connected to a spool or other device for shortening the effective length of the suture. In this example, the tube 360' may have a length substantially less than its circumference.

Presently Preferred Implementation

Many alternative structures can be used to implement the suture tying method described above, including manuallypowered, electrically-powered, and hydraulically or pneumatically-powered devices. The following discussion presents one such structure by way of example, and not by way of limitation.

The term "distal" in this text is used to indicate far from the user and "proximal" close to the user.

The preferred embodiment of the instrument includes two parts: a main piece 100, and a modular piece 300 (FIGS. 1a, 1b).

Figure 2G:
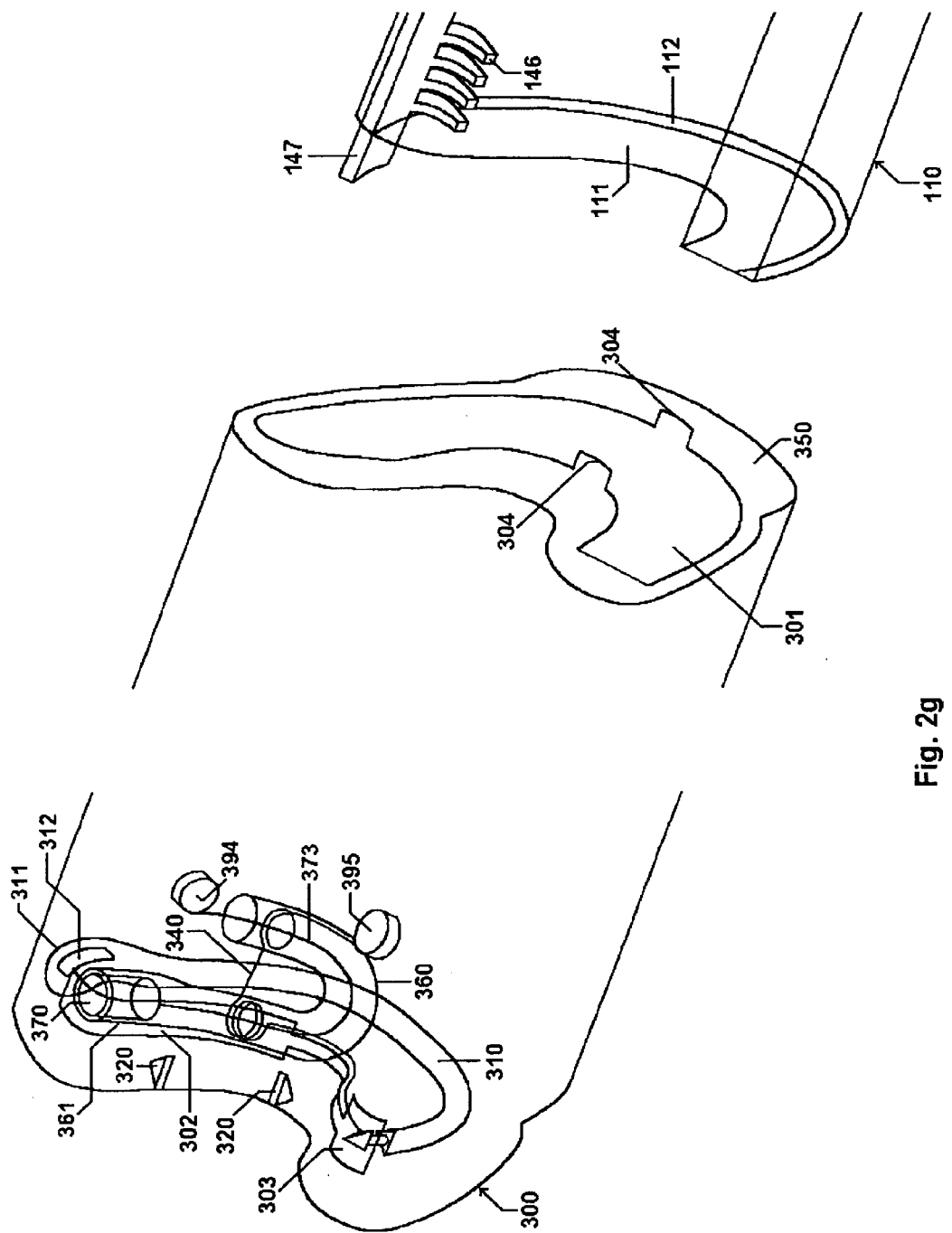
FIG. 2g is a perspective view of selected components of the embodiment of FIGS. 1a and 1b.
Figure 2H:
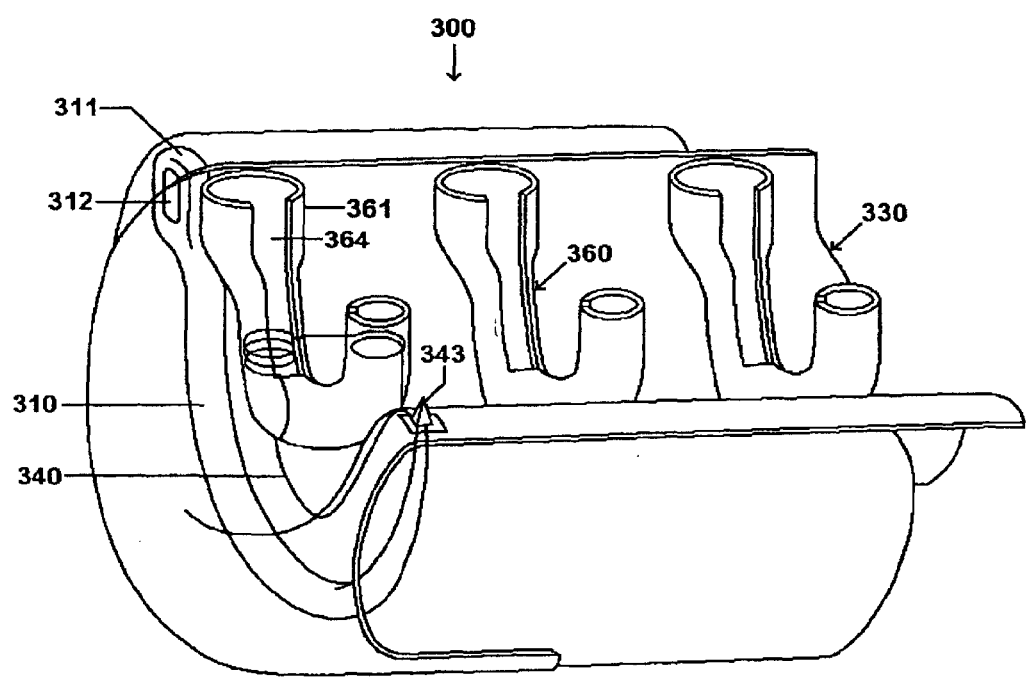
FIG. 2h is an enlarged perspective view showing the relationship between the suture delivery system of FIG. 2f and the needle guide of FIG. 2b.

The modular piece 300 carries a curved needle 310, two small blades 320, and suture assemblies that are mounted on a movable flexible support element 330 (FIGS. 2a–2h). The support element surrounds the needle on three sides (the concave side, the distal lateral side, and the convex side) and moves around the needle (FIG. 2h).

The two small blades are positioned at the tip of the modular unit (FIG. 2g). They stay parallel to the longitudinal axis of the support element. The needle is a semicircle (FIG. 2b). One end of the needle has a handle 311, which has a hole 312 to accept the tip of a crank 147 (FIG. 1a). It steps back to a larger diameter than the needle. A gripping element 370 is positioned in front of the handle of the needle in its primary position. The needle is in a wide enough canal 315 to also accommodate the handle of the needle so that both the needle and the handle can move along it. The canal has an open end 316, where the tip 314 of the needle rests, and a slot 317 along the side facing the crank 147. The end of the suture 342 coming overhead the needle tip has an enlarged element 343 configured to be caught by the tip of the needle and to facilitate gripping by the gripping element described below. When the needle is driven all the way along the canal, the tip 314 together with the caught end of the suture enters into the gripping element 370.

The enlarged element 343 of the suture and the tip 314 of the needle can take many forms. In the example of FIG. 2c, the enlarged element 343 fits within a slot 313 in the needle tip 314. In the example of FIG. 2d, the enlarged element 343' fits on a post that forms the needle tip 314', and it is the enlarged element 343' that forms the piercing edge of the needle. In the example of FIG. 2e, the enlarged element 343" is pierced by the sharpened needle tip 314", and the tip 314" forms the piercing edge of the needle.

Sutures are each placed on the support element 330 in relation to a respective U-shaped tube or canal 360, a gripping element 370 and two spools 394, 395, all of which will be referred to as a suture assembly (FIG. 2f). In other embodiments, the suture assembly may not include spools and it may include other types of canals and gripping elements.

The U-shaped canals 360 are positioned on the support element so that their legs point in the opposite direction to the needle tip (FIG. 2h). The tip 361 of the canal's distal leg has a larger diameter then the rest of the canal and accommodates the gripping element. This part of the U-shaped canal is situated at the recess created by the handle of the needle stepping back to a larger diameter than the needle. The U-shaped canal has a slot 363 along its shorter curve and an open roof 364 for a certain distance from the tip of its distal leg (FIG. 2f). The widths of these openings 363, 364 are smaller than the shorter diameter of the U-shaped canal 360. Transverse slits 365 on the legs of the U-shaped canals allow the blades 320 to pass through.

At its primary position, the gripping element 370 rests at the tip of the distal leg 361 of the U-shaped canal (FIG. 2g). It is cylindrically shaped and made of a compressible material, which is supported with an embedded spiral wire 371 (FIG. 2a). It has also a slit 372 where the tip of the needle together with the enlarged element 343 and the associated end 342 of the suture enters. The spiral wire goes to the top of the gripping element 370, and the other end comes out as a line 373 from the other end. This line 373 follows the U-shaped canal 360 and is attached to a spool 394 at the other end of the U-shaped canal 360. When it is wound up, the line 373 pulls the gripping element 370 through the smaller diameter part of the U-shaped canal 360 to increase its gripping capability.

There are grooves 366 carved on the walls of the U-shaped canal (FIG. 2f). These grooves make spirals on the inside walls of the legs of the U-shaped canal 360. The spiral grooves have a selected number of turns on each leg depending on the knot type, e.g., one turn in each leg for a square knot and two turns in the distal leg and one in the proximal leg for a surgeon's knot. The sutures 340 are laid in these grooves 366 (one suture for each U-shaped canal 360). The grooves are covered with a thin layer of a frangible material. This thin layer of material (that is easily torn when the suture is pulled) contains the sutures within the grooves and lets the gripping element glide through the tube without tangling. In its primary position, a suture is disposed in a "U" shape reverse to and partially overlapping with the U-shaped canal (FIG. 3a). One end 342 of the suture is aligned with the needle tip and the other end 341 is attached to a second spool 395 which is level with the first spool 394 in the proximal-to-distal direction and is on the other side of the U-shaped canal.

The support element 330 is flexible and can be moved around the needle 310 (FIG. 2h). It carries multiple suture assemblies. The modular piece 300 has two openings 302, 303 in addition to the one 301 that accepts the nozzle 110 (FIG. 2g). One of the openings 302 is aligned with the open roofed part of the U-shaped canal 364, and the other 303 is aligned with the needle tip. A slot connects these two openings.

Also, there are several openings on the floor of the support element for different purposes (FIG. 2f). There is an opening 331 in between the U-shaped canal legs to accept a spacer 380 when the spacer is raised with its platform 383 from within the nozzle of the main piece. The spacer is a dome shaped bar that stands perpendicular to its platform. There are two holes 332 underneath the spools to accept two corresponding spool drivers 390, 391 when they are raised with their platform 392 from within the nozzle of the main piece. The openings 334 that allow the needle to pass are also where the enlarged ends 343 of the sutures are releasably held. Finally there are openings 333 to accept the cogs of the cogwheels 410, which advance the support element. Each time the support element is advanced it brings a new suture assembly in front of the needle on the concave side and takes away the used assembly. The used assemblies are stored in the storage space 350 of the modular piece, which is the space turning around the needle and continuing at the convex side of the needle and the nozzle (FIG. 2g).

The overall shape of the modular piece 300 resembles a glove finger and is worn on the nozzle of the main piece 110 from distal to proximal direction and snugly fits on it (FIGS. 1, 2g). A clip mechanism 304 holds the modular piece attached to the main piece (FIG. 2g).

The main piece 100 includes a handle 120, a body 130 and a nozzle 110, and it carries the operating elements and their related pieces. Some pieces are common for some operating elements.

The nozzle is elongated in the preferred embodiment for endoscopic use. The cross-section of the nozzle perpendicular to its long axis is curved conforming to the shape of the needle. A separator extending along the nozzle divides it into inner 111 and outer 112 spaces (FIG. 2*g*).

The outer space 112 is an empty space allowing a crank 147 to sweep from one end to the other and back to its primary position.

Figure 4:
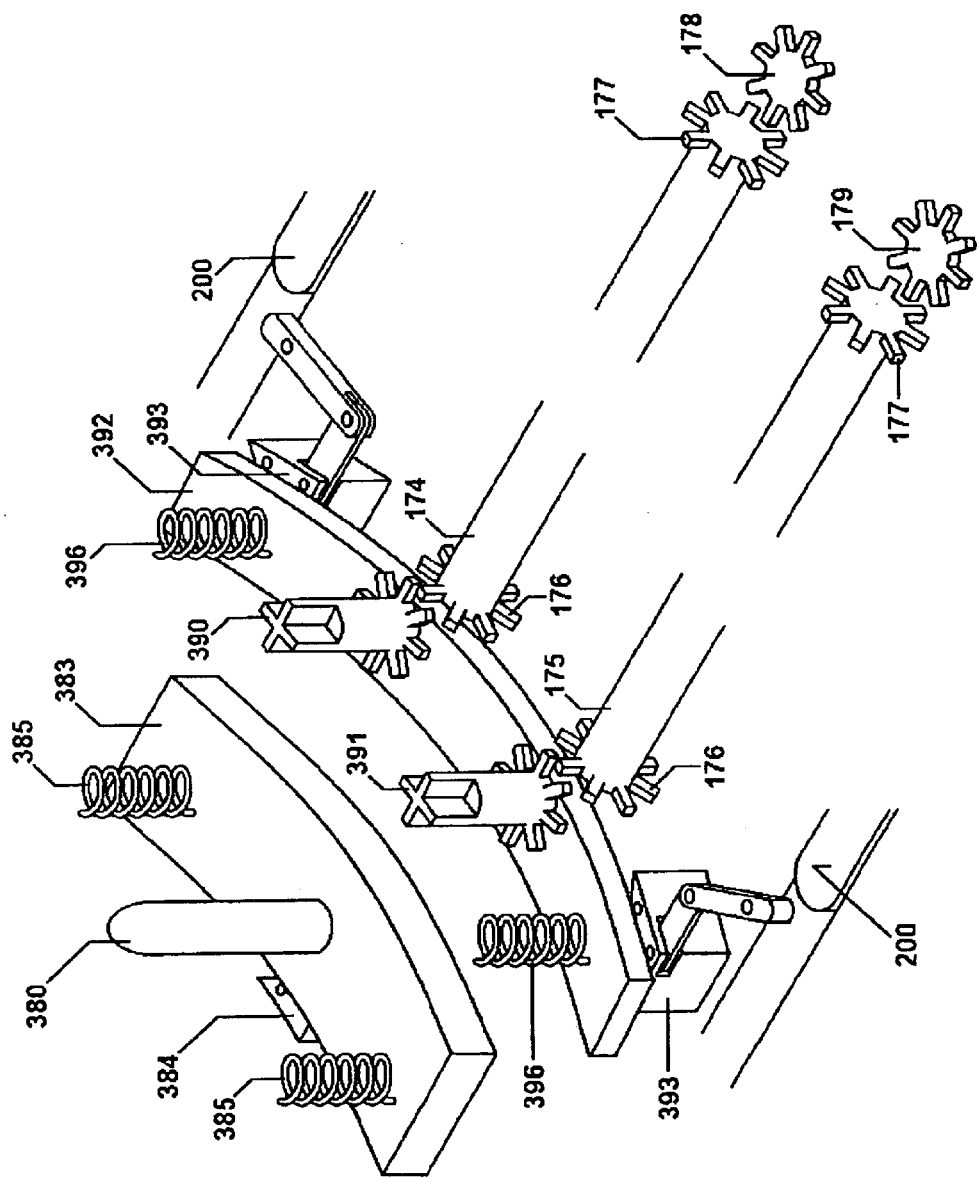
FIG. 4 is a perspective view of components of the embodiment of FIG. 1a that operate to tighten knots in the sutures.

The crank 147 protrudes from the nozzle to enter in the hole 312 at the needle's handle when modular piece is connected (FIG. 2*g*). It has also four processes 146 protruding into the inner space of the nozzle. The inner space contains two spool drivers 390, 391 and a spacer on two separate platforms 392, 383 (FIG. 4). The spacer platform 383 is distal to the spool driver platform 392. Two rotors 174, 175, which rotate the spool drivers, also extend along the nozzle in the inner space. While pushing the needle, the rotation of the crank 147 also raises the platforms of the spool drivers and the spacer by elevating and pushing the supporting blocks 384, 393 under them through its processes 146 extending into the inner nozzle space 111. These platforms 383, 392 are biased separately by springs 385, 396 when the blocks are pushed back to their first position.

Advancing means including cogwheels 410 placed in the nozzle propel the support element for a certain distance each time the primary actuator 121 is released (FIG. 2*g*). An arm 200 that can rotate the cogwheels in only one direction after pushing the supporting blocks of the spool driver platform accomplishes this. These cogwheels are oval so that they only temporarily protrude out of the nozzle when rotated.

Figure 5B:
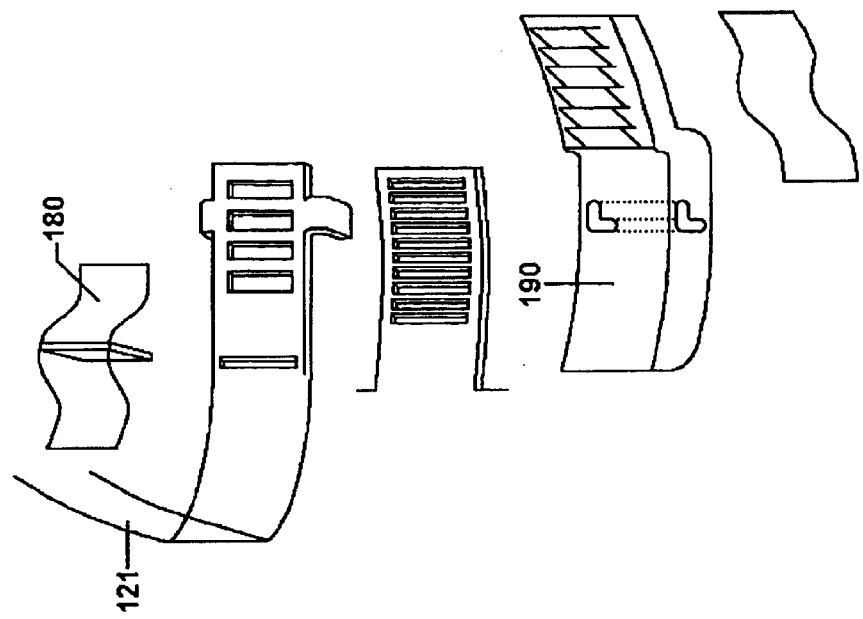
Figure 5A:
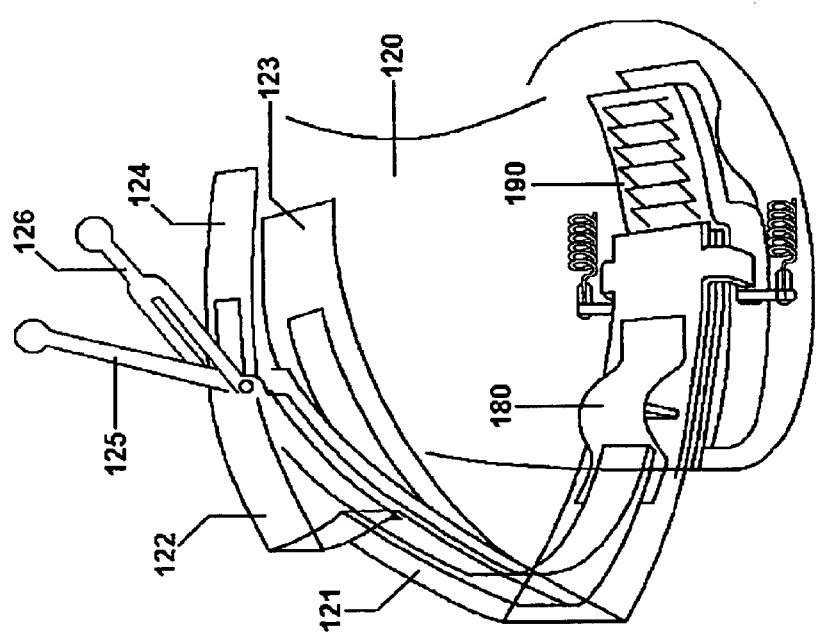

The handle 120 has two actuators: primary 121 and secondary 122 (FIG. 5*a*). They work against springs 123, 124. When flexed, the. primary actuator 121 pushes a multiple piece shaft, which in turn moves the crank 147 and rotates the rotors of the first and the second spools. Due to a serrated ratchet track 190, the actuator 121 holds its flexed or depressed position when it is released. During its flexion, the actuator 121 also flexes the secondary actuator 122 passively. This makes the secondary actuator able to take over the pushing of the shaft further from where the primary actuator leaves off. Activation of the secondary actuator locks the primary actuator and pushes the shaft for a certain distance. Upon its release, after having been flexed, the secondary actuator 122 releases the primary actuator 121, which then returns to its original position. As it returns, the primary actuator lowers the spool driver platform to its primary level and propels the support element, thereby indexing a next suture assembly into position in alignment with the needle.

Figure 6A:
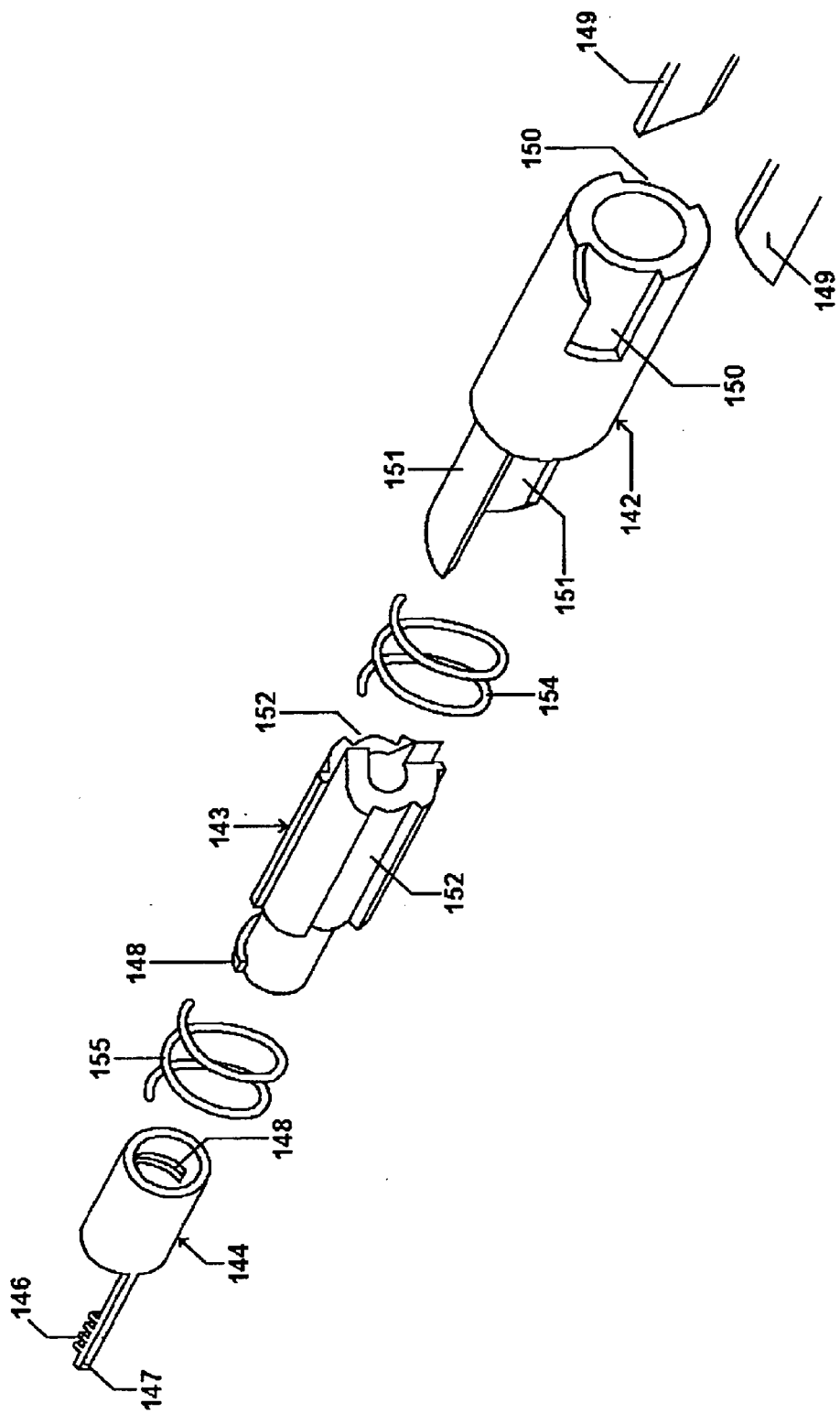

The shaft includes five cylindrically shaped structures 140, 141, 142, 143, 144 longitudinally placed in a single line in the body (FIGS. 6*a*, 6*b*). The distal three 142, 143, 144 and the proximal one 140 are hollow. When they are numbered from proximal to distal, number one 140, two 141 and four 143 can only be advanced, number three 142 can be advanced and rotated, and number five 144 can only be rotated. The crank 147 is an attachment of the fifth cylinder and protrudes in the same direction as the nozzle.

When they are at their primary position and the primary actuator begins to flex, number one through four cylinders are pushed forward by way of an extension 125 (FIG. 5*a*) entering into the first cylinder through a cleft on the wall 157. By a screw mechanism 148 number five 144 and therefore the crank 147 start to rotate. It can be rotated to make only half a circle, being dependent on the length of the screw thread and the corresponding groove and the limited longitudinal movement of the fourth cylinder. The length of this longitudinal movement equals the length of the restraining columns 149 fitting into the corresponding grooves on the sides of the third cylinder 150 that prevent it from rotating. When the third cylinder is relieved from this restraint, it starts to rotate until its two processes 151, which originally push the fourth cylinder, enter into grooves 152 at the outer sides of the fourth cylinder. This prevents the fourth and hence the fifth cylinder from being pushed any farther and the fourth cylinder is then moved by a spring 155. This motion rotates the fifth cylinder in reverse direction because of the unscrewing action. The length of the third cylinder's processes 151 and the fourth cylinder's grooves 152 allow further advancement of the first, second and third cylinders without disturbing the fourth and the fifth. This advancement causes two toothed bars 170, 171 of unequal length to rotate the horizontal cogwheels 178, 179, which in turn rotate the rotors 174, 175 (FIGS. 4 and 6*b*). The rotors cannot move in the proximal-distal direction. At their distal and proximal ends the rotors have cogwheels 176, 177 that stay in the coronal plane. The distal cogwheels 176 of the rotors rotate the spool drivers 390, 391, and the proximal cogwheels 177 are rotated by the two horizontal cogwheels 178, 179. The two-toothed bars 170, 171 (FIG. 6*b*) are two processes of the distal flat surface of the second cylinder. Therefore, pushing the second cylinder causes the spools to rotate (FIGS. 4, 6*b*). The difference in the lengths of the toothed bars determines the starting time of the spools' rotations relative to each other. When the end of the suture 342 is introduced into the gripping element. 370, the first spool's rotor 174 (which winds the suture carrier line 373) starts rotating, and it stops when the other rotor 175 starts rotating. A process 172 on the side of the longer toothed bar 170 disconnects the corresponding horizontal cogwheel 178 from its rotor 174. This process 172 of the longer toothed bar 170 is at the same proximal-to-distal level with the tip of the shorter toothed bar 171 (FIG. 6*b*).

When the user assesses the tension within the suture loop that passes through the tissue as appropriate, he stops flexing the primary actuator. This stops the rotation of the second spool 391 and hence the winding process, but the primary actuator 121 is not released due to the serrated ratchet track 190.

Then the user starts flexing the secondary actuator. This action prevents the primary actuator from further flexion by pushing a stopper 180, which fixes the primary actuator at its current position and also overrides the serrated ratchet track (FIGS. 5*a*, 5*b*).

A part of the second cylinder 156 is inside the first cylinder and it can be moved for a certain distance within the first cylinder. There is a spring 153 inside the first cylinder for pushing this part of the second cylinder and hence the second cylinder along this distance (FIG. 6*b*). In its primary position, an extension 126 of the secondary actuator blocks this spring by conveying the opposing force of the spring of the secondary actuator 124. Note that the primary function of this spring of the secondary actuator is to restore the secondary actuator to its starting position when it is released.

The first cylinder is advanced by the primary actuator during its flexion together with the other cylinders that can be advanced 141, 142, 143, and cannot go backward unless the primary actuator is released. Therefore the secondary actuator cannot move the first cylinder.

Flexing the secondary actuator lets the spring in the first cylinder 153 exert its force on the second cylinder and push it for a predetermined distance starting from where the primary actuator left the second cylinder. This distance is a certain distance because after the loop 345 is tightened to the desired degree the length of pulling distance required to tighten the loop 346 is known (FIG. 3*e*).

When activated by flexing the secondary actuator, the system pushes on a mechanism 160 on the wall of the first cylinder before propelling the second cylinder. The mechanism (FIG. 6*c*) pushes a string 161 perpendicular to the longitudinal axis to shorten the string in the longitudinal direction. This shortening is translated first to reconnection of the disconnected horizontal cogwheel 178 with the corresponding rotor 174 and then to the downward motion of the spacer's platform. Therefore, with the flexion of the secondary actuator the two rotors simultaneously wind to reduce the size of the loop 346 while keeping the tension in the loop 345 constant. When the secondary actuator is released it is restored to its original position by a spring 124. When it is restored, it lets the stopper 180 that it has pushed to lock the primary actuator to recover and thus releases the primary actuator. Then the primary actuator is restored to its original position by its spring 123 and this movement pushes the supporting blocks under the spool driver platform to lower the platform and moves the support element forward by sequentially pushing the arm 200.

Release of the primary actuator also allows a spring 154, which becomes unopposed, to restore the third and hence the second and the first cylinders to their original positions. Meantime, the reducing spring of the secondary actuator loads the spring in the first cylinder.

In the illustrated example, the user initiates first and second triggering events by squeezing the first and second actuators, thereby initiating the various operations described above. In this example, the user only squeezes the second actuator once the tension on the suture loop that passes through the tissue is at the desired level. Alternatively, the second triggering event may be initiated automatically when the tension on the suture loop that passes through the tissue reaches a pre-set level.

Because the spacer 380 has a tapered top, and the spacer 380 is progressively lowered as the second loop 346 is tightened (after the second triggering event), the spacer maintains tension in the first loop 345 as the second loop 346 is tightened.

The main piece can be shaped differently, as appropriate for the application. For example, the operating portion of the main piece can be made to rotate over an arc of e.g. 180° to make use of the main piece more comfortable when the modular piece is inverted or oriented at some other angle in use.

As used here, the term "set" means one or more. The term "coupled with" is intended broadly to include direct coupling (when a first element engages a second element directly) and indirect coupling (when a first element is coupled to a second element by one or more unnamed intermediate elements).

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for applying and tying a surgical suture, said method comprising:
   (a) providing a suturing device comprising a handle at one end and at least one needle and at least one suture at the other end;
   (b) in response to at least one triggering event at the handle, performing the following acts automatically at the other end of the suturing device by the suturing device;
   (b1) passing a portion of the suture through tissues to be held together with the needle; then
   (b2) forming a knot in the suture without preparatory manual looping of the suture by a user.

2. The method of claim 1 further comprising:
   (c) cutting the suture on both sides of the knot with the suturing device after (b).

3. The method of claim 2 wherein (c) is performed automatically in response to a triggering event.

4. The method of claim 3 wherein the suturing device provided in (a) comprises a plurality of sutures, and wherein the method further comprises:
   (c) moving a next one of the sutures into alignment with the needle after (b).

5. The method of claim 4 wherein (c) is performed automatically in response to a triggering event.

6. The method of claim 1 further comprising:
   (b3) tightening the knot with the suturing device.

7. The method of claim 6 wherein (b4) is performed automatically in response to a triggering event.

8. A method for applying and tying a surgical suture, said method comprising:
   (a) providing a suturing device comprising a handle at one end and a suture delivery system at the other end, said suture delivery system comprising:
      a suture wrapped in a set of coils, said suture comprising a first end and a second end;
      a suture carrier comprising a line passing through at least one of the coils, said line comprising a first end and a second end;
      a needle guide; and
      a needle slideably mounted in the needle guide; and then
   (b) performing the following acts:
      (b1) passing the second end of the suture with the needle through tissues to be secured together; then
      (b2) gripping the second end of the suture with the suture carrier near the second end of the line; and then
      (b3) moving the second end of the suture through said at least one of the coils with the suture carrier.

9. The method of claim 8 wherein the suture delivery system of (a) comprises a tube, and wherein the suture is wrapped around the tube prior to performing (b).

10. The invention of claim 9 further comprising:
    (b4) tightening the first and second ends of the suture, wherein the tightening of (b4) causes the suture to break through the tube.

11. The method of claim 9 wherein the tube provided in (a) comprises first and second legs and a bight portion arranged in a U-shape, and wherein the suture is wrapped around both legs of the tube.

12. The method of claim 11 further comprising:
    (b4) tightening the first and second ends of the suture; and
    (c) placing at least one spacer between the bight portion and the suture and between the first and second legs prior to (b4).

13. A method for applying and tying a surgical suture, said method comprising:
    (a) providing a suturing device comprising a handle at one end and a suture delivery system at the other end, said suture delivery system comprising:
       a suture wrapped in a set of coils, said suture comprising a first end and a second end;
       a gripping element configured to grip the second end of the suture;
       a needle guide; and
       a needle slideably mounted in the needle guide; and then
    (b) performing the following acts:
       (b1) passing the second end of the suture with the needle through tissues to be secured together; then
       (b2) passing the second end of the suture through said at least one of the coils with the needle; and then
       (b3) gripping the second end of the suture with the gripping element.

14. The method of claim 8 or 13 further comprising:
(b4) tightening the first and second ends of the suture.

15. The method of claim 14 further comprising:
(c) placing at least one spacer in at least one loop of the suture prior to (b4).

16. The method of claim 14 wherein (b4) is performed automatically in response to a triggering event.

17. The method of claim 14 wherein (b4) comprises:
(b4a) pulling at least one of the ends of the suture to tighten a first loop of the suture but not a second loop of the suture; and then
(b4b) pulling at least one of the ends of the suture to tighten the second loop of the suture.

18. The method of claim 17 further comprising;
progressively reducing an effective width of the spacer during (b4b).

19. The method of claim 17 further comprising:
(b4c) automatically initiating (b4b) when tension in the first loop reaches a threshold value during (b4a).

20. A method for applying and tying a surgical suture, said method comprising:
(a) providing a suturing device comprising a handle at one end and a suture delivery system at the other end, said suture delivery system comprising:
a suture having a partially tied knot comprising at least one loop, said suture comprising a first end and a second end;
a suture carrier comprising a line passing through the loop of the partially tied knot, said line comprising a first end and a second end;
a needle guide; and
a needle slideably mounted in the needle guide; and then
(b) peforming the following acts:
(b1) passing the second end of the suture with the needle through tissues to be secured together; then
(b2) gripping the second end of the suture with the suture carrier near the second end of the line; and then
(b3) moving the second end of the suture through the loop with the suture carrier.

21. A method for applying and tying a surgical suture, said method comprising:
(a) providing a suturing device comprising a handle at one end and a suture delivery system at the other end, said suture delivery system comprising:
a suture having a partially tied knot comprising at least one loop, said suture comprising a first end and a second end;
a gripping element configured to grip the second end of the suture;
a needle guide; and
a needle slideably mounted in the needle guide; and then
(b) performing the following acts:
(b1) passing the second end of the suture with the needle through tissues to be secured together; then
(b2) passing the second end of the suture through the loop with the needle; and then
(b3) gripping the second end of the suture with the gripping element.

22. The method of claim 20 or 21 further comprising:
(b4) tightening the first and second ends of the suture.

23. The method of claim 22 wherein (b4) comprises:
(b4a) pulling at least one of the ends of the suture to tighten a first loop of the suture but not a second loop of the suture; and then
(b4b) pulling at least one of the ends of the suture to tighten the second loop of the suture.

24. The method of claim 23 further comprising:
(b4c) automatically initiating (b4b) when tension in the first loop reaches a threshold value during (b4a).

25. The method of claim 22 wherein (b4) is performed automatically in response to a triggering event.

26. The method of claim 13, 20 or 21 wherein the suture delivery system of (a) comprises a tube, and wherein the suture is wrapped around the tube prior to performing (b).

27. The invention of claim 26 further comprising:
(b4) tightening the first and second ends of the suture, wherein the tightening of (b4) causes the suture to break through the tube.

28. The method of claim 8, 13, 20 or 21 wherein (b) forms a knot in the suture, and wherein the method further comprises:
(c) cutting the suture on both sides of the knot with the suturing device after (b).

29. The method of claim 8, 13, 20 or 21 wherein the suture delivery system provided in (a) comprises a plurality of sutures, and wherein the method further comprises:
(c) moving a next one of the sutures into alignment with the needle after (b).

30. The method of claim 8, 13, 20 or 21 wherein (b) is performed automatically in response to at least one triggering event.

31. A method for applying and tying a surgical suture, said method comprising:
(a) providing a suturing device comprising a handle at one end and at least one needle and at least one suture at the other end;
(b) in response to a first triggering event at the handle, performing the following acts at the other end of the suturing device:
(b1) passing a portion of the suture through two tissues to be held together with the needle; then
(b2) forming at least first and second loops in the suture; and then
(b3) tightening the first loop;
(c) in response to a second triggering event at the handle, performing the following acts at the other end of the suturing device;
(c1) tightening the second loop; and then
(c2) cutting the suture on both sides of the second loop.

32. The method of claim 31 wherein the suturing device provided in (a) comprises a plurality of sutures, and wherein (c) further comprises:
(c3) moving a next one of the sutures into alignment with the needle.

33. A method for applying and tying a surgical suture, said method comprising:
(a) providing a suturing device comprising a handle at one end and at least one needle and at least one suture at the other end, each said suture comprising a partially tied knot comprising a second loop;
(b) in response to a first triggering event at the handle, performing the following acts at the other end of the suturing device:
(b1) passing a portion of the suture through two tissues to be held together with the needle; then
(b2) forming at least a first loop in the suture and then
(b3) tightening the first loop;

(c) in response to a second triggering event at the handle, performing the following acts at the other end of the suturing device;
  (c1) tightening the second loop; and then
  (c2) cutting the suture on both sides of the second loop.

34. The method of claim 33 wherein the suturing device provided in (a) comprises a plurality of sutures, and wherein (c) further comprises:

(c3) moving a next one of the sutures into alignment with the needle.

35. The method of claim 32 or 34 wherein (c3) is performed automatically in response to a triggering event.

* * * * *